United States Patent [19]
Rinaldi et al.

[11] Patent Number: 5,436,253
[45] Date of Patent: Jul. 25, 1995

[54] PYRIDONECARBOXYLIC ACID DERIVATIVES AND MYCOTIC INFECTIONS

[75] Inventors: Michael G. Rinaldi; Annette W. Fothergill, both of San Antonio, Tex.

[73] Assignee: Daiichi Pharmaceutical Co., Ltd., Tokyo, Japan

[21] Appl. No.: 117,662

[22] Filed: Sep. 8, 1993

[51] Int. Cl.⁶ ............................................. A61K 31/44
[52] U.S. Cl. ................................................. 514/312
[58] Field of Search ........................................ 514/312

[56] References Cited

PUBLICATIONS

Petrou et al., Drugs Exptl. Clin Res. XIV (1) 9–18 (1988).

*Primary Examiner*—Marianne M. Cintins
*Assistant Examiner*—Phyllis G. Spivack

[57] ABSTRACT

The invention relates to a method for enhancing the antimycotic activity of an antimycotic agent comprising using a pyridonecarboxylic acid derivative.

2 Claims, No Drawings

PYRIDONECARBOXYLIC ACID DERIVATIVES AND MYCOTIC INFECTIONS

FIELD OF THE INVENTION

The instant invention relates to the use of pyridonecarboxylic acid derivatives to enhance the antimycotic effect of an antimycotic agent.

BACKGROUND OF THE INVENTION

Quinoline derivatives having a condensed pyridonecarboxylic acid skeleton and substitution of the 1-position thereof with a cyclopropyl group are known as synthetic antimicrobial agents.

It is further known that 1-cyclopropylquinolone derivatives having a fluorine atom at the 2-position of the cyclopropyl group in a cis-configuration with the pyridonecarboxylic acid moiety also exhibit potent antimicrobial activity, as disclosed in EP-A 341493, which corresponds to JP-A-90-231475 (The terms "EP-A" and "JP-A" as used herein mean an "unexamined published European patent application" and an "unexamined published Japanese patent application", respectively). Said derivatives not only have potent antimicrobial activity but also improved safety.

A variety of antifungal agents have been developed and are in use, see, for example, The Merck Index.

SUMMARY OF THE INVENTION

The instant invention relates to a method of enhancing the antimycotic effect of an antimycotic agent comprising using in combination therewith a pyridonecarboxylic acid derivative. Preferably the pyridonecarboxylic acid derivative is administered simultaneously with or subsequently to administration of an antimycotic agent to potentiate the effect of said antimycotic agent.

An example of a suitable pyridonecarboxylic acid derivative is an $N_1$-(1,2-cis-2-halogenocyclopropyl)-substituted pyridonecarboxylic acid derivative represented by formula (I):

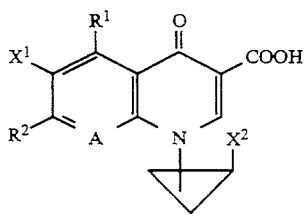

wherein $R^1$ represents a hydrogen atom, an amino group, an alkylamino group of from 1 to 3 carbon atoms, a hydroxyl group or a thiol group;

$R^2$ represents a cyclic amino group represented by the following formula:

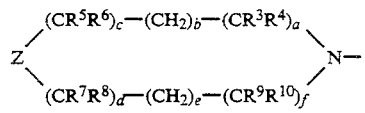

wherein a, b, c, d, e and f each independently represents an integer, 0 or 1, and at least one of a, b, c, d, e, or f is 0;

$R^3$, $R^4$, $R^5$, $R^6$, $R^7$, $R^8$, $R^9$ and $R^{10}$ independently represents hydrogen atoms or alkyl groups of from 1 to 3 carbon atoms, and $R^5$ may, together with $R^6$, form a methylene chain of from 2 to 5 carbon atoms, and $R^5$ may, together with $R^9$, form a methylene chain of from 2 to 4 carbon atoms;

Z represents $>CHR^{11}$, $>NR^{12}$, $>C=NOR^{13}$, an oxygen atom or a sulfur atom;

wherein $R^{11}$ represents a hydrogen atom, an amino group, a monoalkylamino group of from 1 to 6 carbon atoms, a dialkylamino group containing from 1 to 6 carbon atoms per alkyl, a tert-butoxycarbonylamino group, a benzyloxycarbonylamino group, a hydroxyl group, an alkoxyl group of from 1 to 6 carbon atoms, a hydroxyalkyl group of from 1 to 6 carbon atoms or a 2-aminoethyl group;

$R^{12}$ represents a hydrogen atom, an alkyl group of from 1 to 6 carbon atoms, a hydroxyalkyl group of from 1 to 6 carbon atoms, a haloalkyl group of from 1 to 6 carbon atoms, a formyl group or an alkylcarbonyl group of from 2 to 7 carbon atoms;

$R^{13}$ represents a hydrogen atom or an alkyl group of from 1 to 6 carbon atoms;

A represents C-$X^3$ or a nitrogen atom;

$X^1$ and $X^2$, which may be the same or different, each represents a halogen atom;

and $X^3$ represents a halogen atom, an alkyl group of from 1 to 6 carbon atoms, an alkoxy group of from 1 to 6 carbon atoms, a cyano group, a trifluoromethyl group or a hydrogen atom;

or a pharmaceutically acceptable salt thereof.

Specifically implicit in the compounds represented by formula (I), and salts thereof, are those wherein $R^2$ is a cyclic amino group which may be substituted; those wherein $R^2$ is a 4-membered to 7-membered cyclic amino group which may be substituted with a hydroxyl group, an alkyl group having from 1 to 6 carbon atoms, or a substituted or unsubstituted amino group; those wherein $R^2$ is a pyrrolidinyl, piperidinyl, piperazinyl, diazabicycloheptyl or diazabicyclooctyl group; those wherein $R^2$ is a cyclic amino group comprising a single stereoisomer; those wherein $R^2$ is a 3-aminopyrrolidinyl group; those wherein $R^2$ is a 7-amino-5-azaspiro[2.4-]heptan-5-yl group; and those wherein $X^2$ is a fluorine atom.

More specifically, the compounds according to the instant invention include 7-[3-(S)-amino-1-pyrrolidinyl]-6-fluoro-1-(1,2-cis-2-fluorocyclopropyl)-4-oxo-1,4-dihydroquinoline-3-carboxylic acid, 7-[3-(S)-amino-1-pyrrolidinyl]-8-chloro-6-fluoro-1-(1,2-cis-2-fluorocyclopropyl)-4-oxo-1,4-dihydroquinoline-3-carboxylic acid, 7-[7-amino-5-azaspiro-[2.4]heptan-5-yl]-8-chloro-6-fluoro-1-(1,2-cis-2-fluorocyclopropyl)-4-oxo-1,4-dihydroquinoline-3-carboxylic acid, 7-[8-amino-6-azaspiro[3.4]octan-6-yl]-8-chloro-6-fluoro-1-(1,2-cis-2-fluorocyclopropyl)-4-oxo-1,4-dihydroquinoline-3-carboxylic acid, 7-[4-amino-3,3-dimethyl-1-pyrrolidinyl]-8-chloro-6-fluoro-1-(1,2-cis-2-fluorocyclopropyl)-4-oxo-1,4-dihydroquinoline-3-carboxylic acid, 5-amino-7-[3-(S)-amino-1-pyrrolidinyl]-6,8-difluoro-1-(1,2-cis-2-fluorocyclopropyl)-4-oxo-1,4-dihydroquinoline-3-carboxylic acid, 7-[4-(S)-amino-2-(S)-methyl-1-pyrrolidinyl]-6-fluoro-1-(1,2-cis-2-fluorocyclopropyl)-4-oxo-1,4-dihydroquinoline-3-carboxylic acid, 7-[3-(R)-[1-(S)-aminoethyl]-1-pyrrolidinyl]-8-chloro-6-fluoro-1-(1,2-cis-2-fluorocyclopropyl)-4-oxo-1,4-dihydroquinoline-3-carboxylic acid, 7-[3-amino-4-methyl-1-pyrrolidinyl]-6-fluoro-1-(1,2-cis-2-fluorocyclopropyl)-8-methoxy-4-oxo- 1,4-dihydroquinoline-3-carboxylic acid, 7-[4-(S)-amino-2-(S)-methyl-1-pyrrolidinyl]-6-fluoro-1-(1,2-cis-2-fluorocyclopropyl)-8-methyl-4-oxo-1,4-dihydroquinoline-3-carboxylic acid, 5-amino-7-[7-amino-5-azaspiro[2.4]heptan-5-yl]-6,8-difluoro-1-(1,2-cis-2-fluorocyclopropyl)-4-oxo-1,4-dihydroquinoline-3-carboxylic acid; or a pharmaceutically acceptable salt thereof.

The instant invention also relates to a manufacture comprising an antimycotic agent and a pyridonecarboxylic acid derivative.

DETAILED DESCRIPTION OF THE INVENTION

The instant invention relates to the use of a pyridonecarboxylic acid derivative and an antimycotic to control mycotic growth, to act mycostatically, to act mycocidally and to treat conditions characterized by mycotic presence or growth. Generally, the pyridonecarboxylic acid derivatives have little or no antimycotic activity but potentiate and often synergistically increase the antimycotic activities of an antimycotic agent.

As to the pyridonecarboxylic acid derivative, in formula (I), when A represents C-X$_3$, and when X$^3$ represents a halogen atom, X$^1$ and X$^3$ each preferably represents a fluorine atom or a chlorine atom; and X$^2$ preferably represents a fluorine atom. R$^1$ represents an alkylamino group of from 1 to 3 carbon atoms, an unsubstituted amino group, a hydroxyl group, a thiol group or a hydrogen atom, preferably an unsubstituted amino group, a methylamino group or a hydrogen atom.

R$^2$ represents a cyclic amino group, preferably a 4-membered to 7-membered ring, and more preferably 5-membered or 6-membered cyclic amino group. The cyclic amino group further may contain oxygen atom(s), sulfur atom(s) and/or nitrogen atom(s), as in oxazolidinyl, morpholinyl, thiazolidinyl, thiomorpholinyl, imidazolidinyl, pyrazolidinyl and piperazinyl groups. Of cyclic amino groups, preferred groups are a pyrrolidinyl group and a piperazinyl group.

The cyclic amino group may have substituents, such as a polar group (e.g., a substituted or unsubstituted amino group, a substituted or unsubstituted aminoalkyl group, a 5-substituted-2-oxo-1,3-dioxol-4-ylmethyl group or a hydroxyl group) and a straight chain, a branched chain or cyclic alkyl group having up to 6 carbon atoms. Preferred polar groups are an unsubstituted amino group, an aminomethyl group, a 1-aminoethyl group and a hydroxyl group. Preferred alkyl groups are methyl, ethyl, propyl, gem-dimethyl and gem-dimethyl groups, and further, the gem-alkyl groups preferably may form a cyclopropane or cyclobutane ring which is bonded through a spiro-union to the cyclic amine skeleton. The cyclic amino group further includes a bicyclic amino group composed of cross-linking to 4-membered to 7-membered cyclic amino groups.

Illustrative examples of these cyclic amino groups, particularly containing the second amino moiety, are:

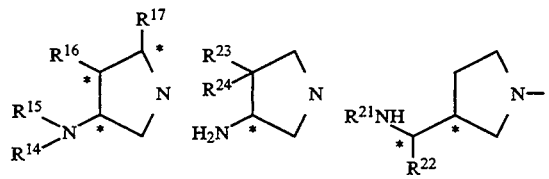

-continued

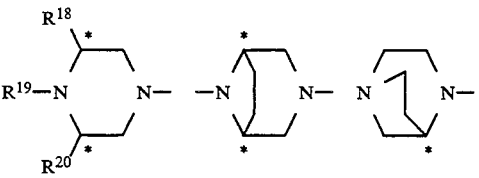

wherein R$^{14}$, R$^{15}$, R$^{16}$ and R$^{17}$, which may be the same or different, each represents a hydrogen atom or an alkyl group having from 1 to 6 carbon atoms; R$^{18}$, R$^{19}$ and R$^{20}$, which may be the same or different, each represents a hydrogen atom or an alkyl group having from 1 to 6 carbon atoms, provided that the case wherein R$^{18}$, R$^{19}$ and R$^{20}$ each represents a hydrogen atom and the case wherein R$^{18}$ and R$^{20}$ each represents a hydrogen atom and R$^{19}$ represents an alkyl group having from 1 to 6 carbon atoms are excluded; R$^{21}$ and R$^{22}$, which may be the same or different, each represents a hydrogen atom or an alkyl group having from 1 to 6 carbon atoms; R$^{23}$ and R$^{24}$, which may be the same or different, each represents a hydrogen atom or an alkyl group having from 1 to 6 carbon atoms, or may be connected to each other to form a 3-membered to 6-membered ring composed of methylene chains; and the asterisk indicates an asymmetric center.

Examples of cyclic amino groups are 3-aminopyrrolidinyl, 3-methylaminopyrrolidinyl, 3-dimethylaminopyrrolidinyl, 3-ethylaminopyrrolidinyl, 3-propylaminopyrrolidinyl, 3-isopropylaminopyrrolidinyl, 3-amino-4-methylpyrrolidinyl, 3-amino-5-methylpyrrolidinyl, 3-amino-4,5-dimethylpyrrolidinyl, 3-methylamino-4-methylpyrrolidinyl, 3-methylamino-5-methylpyrrolidinyl, 3-methylamino-4,5-dimethylpyrrolidinyl, 3-dimethylamino-4-methylpyrrolidinyl, 3-dimethylamino-5-methylpyrrolidinyl, 3-dimethylamino-4,5-dimethylpyrrolidinyl, 3-dimethyl-amino-4-methylpyrrolidinyl, 3-dimethylamino-5-methyl-pyrrolidinyl, 3-dimethylamino-4,5-dimethyl-pyrrolidinyl, 3-methylpiperazinyl, 4-methylpiperazinyl, 3,4-dimethylpiperazinyl, 3,5-dimethylpiperazinyl, 3,4,5-trimethylpiperazinyl, 4-ethyl-3,5-dimethylpiperazinyl, 4-isopropyl-3,5-dimethylpiperazinyl, 3-aminomethylpyrrolidinyl, 3-methylaminomethylpyrrolidinyl, 3-(1-amino)ethylpyrrolidinyl, 3-(1-methylamino)ethylpyrrolidinyl, 3-(1-ethylamino)ethylpyrrolidinyl, 3-(1-amino)propylpyrrolidinyl, 3-(1-methylamino)propylpiperazinyl, 3-aminopyrrolidinyl, 3-amino-4,4-dimethylpyrrolidinyl, 7-amino-5-azaspiro[2.4]heptan-5-yl, 8-amino-6-azaspiro[3.4]-octan-6-yl, 3,4-diazabicyclo[3,2,1]octan-3-yl, 9-methyl-3,9-diazabicyclo[3.2.1]octan-3-yl and 9-ethyl-3,9-diazabicyclo[3.2.1]octan-3-yl.

Additionally preferred cyclic amino groups are piperazine groups, such as alkylpiperazine groups and piperazine groups having a spiro ring.

Examples of cyclic amino groups having substituents other than an amino group are 3-hydroxypyrrolidinyl, 3-mercaptopyrrolidinyl, 3-hydroxy-4-methylpyrrolidinyl, 3-mercapto-4-methylpyrrolidinyl, morpholino, thiomorpholino, 2-methylmorpholino, 2-methylthiomorpholino, 2,6-dimethylmorpholino, 2,6-dimethylthiomorpholino, 2,2-dimethylmorpholino and 2,2-dimethylthiomorpholino groups.

The cyclic amino group is bonded to the 7-position of the pyridonecarboxylic acid skeleton preferably at the nitrogen atom of the cyclic amino group. As a matter of course, it may be bonded at the other atom, i.e., a carbon atom of the cyclic amino group.

The stereoisomerism of the cyclic amine moiety at the 7-position is explained hereinbelow. In cases where a cyclic amine has isomers, if it is reacted in the form of an isomeric mixture with a 1-(1,2-cis-halogenocyclopropyl)quinoline derivative, the resulting quinoline derivative should be a mixture of diasteromers based on the steric relation with the 1,2-cis-2-halogenocyclopropyl group at the 1-position. In that case, therefore, it is necessary that only one of the isomers of the starting amine should be reacted.

The functional group of the cyclic amino group at the 7-position such as amino, hydroxy and thiol groups may be protected by a conventional protective group prior to the substitution with the quinoline skeleton. The examples of such protective groups include alkoxycarbonyl groups, such as t-butoxycarbonyl group, 2,2,2-trichloroethoxycarbonyl group and the like; aralkyloxycarbonyl groups, such as benzyloxycarbonyl group, p-methoxybenzyloxycarbonyl group, p-nitrobenzyloxycarbonyl group and the like; acyl groups, such as acetyl group, methoxyacetyl group, trifluoroacetyl group, chloroacetyl group, pivaloyl group, formyl group, benzoyl group and the like; alkyl or aralkyl groups, such as t-butyl group, benzyl group, p-nitrobenzyl group, p-methoxybenzyl group, triphenylmethyl group and the like; ethers, such as methoxymethyl group, t-butoxymethyl group, 2,2,2-trichloroethoxymethyl group, tetrahydrofuran-2-yl group and the like; silyl groups, such as trimethylsilyl group, isopropyldimethylsilyl group, t-butyldimethylsilyl group, t-butyldiphenylsilyl group, tribenzylsilyl group and the like.

The 1,2-cis-2-halogenocyclopropyl group at the $N_1$-position is described below. Introduction of a halogen atom to the cyclopropyl group, particularly a fluorine atom, reduces the lipophilicity of the whole molecule. It is known that drugs are more likely to be distributed to the central nervous system as lipophilicity thereof increases. The halogen atom to be introduced includes fluorine and chlorine atoms, with a fluorine atom preferred.

It is particularly preferable that the halogen atom and the pyridonecarboxylic acid moiety are cis with respect to the cyclopropane ring. Irrespective of whether the 7-cyclic amino group has stereoisomers or not, the quinoline derivatives of formula (I) have enantiomeric pairs ascribed to the cis-2-halogenocyclopropyl moiety at the 1-position as illustrated below. Potent activity and high safety were observed in either of those enantiomers.

The pyridonecarboxylic acid derivatives according to the instant invention include the respective free acids, acid-addition salts thereof and the salts of the carboxyl group thereof. The acid-addition salts include inorganic acid salts, e.g., hydrochlorides, sulfates, nitrates, hydrobromides, hydroiodides and phosphates; and organic acid salts, e.g., acetates, methanesulfonates, benzenesulfonates, toluenesulfonates, citrates, maleates, fumarates and lactates.

The salts of the carboxyl group may be organic or inorganic and include alkali metal salts, e.g., lithium salts, sodium salts and potassium salts, alkaline earth metal salts, e.g., magnesium salts and calcium salts; ammonium salts, triethylamine salts, N-methylglucamates and tris(hydroxymethyl)aminomethane salts.

Some of the free acids and salts may exist as hydrates thereof.

Esterification of the carboxylic acid moiety of the pyridonecarboxylic acid derivatives of formula (I) gives compounds useful as synthesis intermediates or prodrugs. For example, alkyl esters, benzyl esters, alkoxyalkyl esters, phenylalkyl esters and phenyl esters are useful as synthesis intermediates. Esters which are served easily in the body to form free carboxylic acids are useful as prodrugs. Examples of such esters are acetoxymethyl esters, pivaloyloxymethyl esters, ethoxycarbonyloxy esters, chlorine esters, dimethylaminoethyl esters, 5-indanyl esters, phthalidinyl esters and oxoalkyl esters (e.g., 5-substituted-2-oxo-1,3-dioxol-4-yl-methyl esters and 3-acetoxy-2-oxobutyl esters).

A process for synthesizing the pyridonecarboxylic acid derivatives of formula (I) is disclosed in EP-A 341493 and U.S. Ser. No. 07/610916.

A preferred species within general formula (I), which are also, of course, preferably also within the isomer embodiment or the (S)/(R) acid embodiment are:

7-[7-amino-5-azaspiro[2.4]heptan-5-yl]-8-chloro-6-fluoro-1-(1,2-cis-2-fluorocyclopropyl)-4-oxo-1,4-dihydroquinoline-3-carboxylic acid (DU-6859) or a pharmaceutically acceptable salt thereof;

7-[8-amino-6-azaspiro[3.4]octan-6-yl]-8-chloro-6-fluoro-1-(1,2-cis-2-fluorocyclopropyl)-4-oxo-1,4-dihydroquinoline-3-carboxylic acid or a pharmaceutically acceptable salt thereof; and 7-[4-amino-3,3-dimethyl-1-pyrrolidinyl]-8-chloro-6-fluoro-1-(1,2-cis-2-fluorocyclopropyl)-4-oxo-1,4-dihydroquinoline-3-carboxylic acid or a pharmaceutically acceptable salt thereof.

The instant invention is directed especially to an agent comprising a therapeutically effective amount of, as an active ingredient, at least one $N_1$-(1,2-cis-2-halogenocyclopropyl)-substituted pyridonecarboxylic acid derivative represented by formula (I), or a pharmaceutically acceptable salt thereof, in combination with a pharmaceutically acceptable carrier, where the pharmaceutically acceptable salt is most preferably the hydrochloride, sulfate, phosphate, acetate, methanesulfonate, benzenesulfonate, p-toluenesulfonate, citrate, maleate, fumarate or lactate and an antimycotic agent, and to a method for treating mycotic infections which comprises administering a therapeutically effective amount of $N_1$-(1,2-cis-2-halogenocyclopropyl)-substituted pyridonecarboxylic acid represented by the formula (I) or a pharmaceutically acceptable salt thereof and an antimycotic agent.

Suitable examples of pyridonecarboxylic acid derivatives useable with an antifungal agent to provide an enhanced antimycotic activities are 6-fluoro-1,4-dihydro-4-oxo-3-quinolinecarboxylic acid derivatives, such as norfloxacin (U.S. Pat. No. 4,146,719), ciprofloxacin (U.S. Pat. No. 4,670,444), lomefloxacin (U.S. Pat. No. 4,528,287), DU-6859 or DU-6859a, a sesquihydrate form of DU-6859 (compound 26bb of U.S. Ser. No. 07/610916 and EP 341493-A), fleroxacin (U.S. Pat. No. 4,398,029) and sparfloxacin (EP-221462-A); 9-fluoro-2,3-dihydro-3-methyl-7-oxo-7H-pyrido[1,2,3-de][1,4]benzoxazine-6-carboxylic acid derivatives, such as, ofloxacin (U.S. Pat. No. 4,382,892), levofloxacin (U.S. Pat. No. 5,053,407), DV-7751 (EP-357047-A and U.S. Ser. No. 07/878514) and T-3761 (JP-90-28178-A); and 6-fluoro-1,4-dihydro-4-oxo-1,8-naphthyridine-3-carboxylic acid derivatives, such as, exoxacin (U.S. Pat. No. 4,352,803), tosufloxacin (U.S. Pat. No. 4,704,459), rufloxacin (J. Med. Chem., 30, 465, 1987) and perfloxacin (Infection 12, 294, 1986). Also useable are the compounds AM-1155 (JP-89-16746-A), OPC-17116 (JP-89-230558-A), O-35 (JP-91-95177-A), MAD-441 (Antimicrob. Agents Chemotherap. 1896 (1989) and Y-26611 (JP-90-138278-A).

Also useable in the instant antimycotic formulation are fluorine-containing pyridonecarboxylic acid derivatives represented by the formula (II):

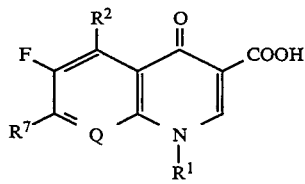

wherein Q is =N— or =C($R^8$)— [$R^8$ being H, F, Cl, an alkyl group having from one to four carbon atoms, an alkoxyl group having from one to four carbon atoms, or $R^8$ together with $R^1$ may form —OCH$_2$CH($R^{81}$)—, —SCH$_2$CH(C$R^{81}$)— or —OCH$_2$N($R^{81}$)— ($R^{81}$ being H or an alkyl group having from one to four carbon atoms) to complete an additional ring]; $R^1$ is a lower alkyl group, a cyclopropyl group, a halocyclopropyl group, a haloethyl group, a vinyl group, a phenyl group or a halophenyl group, $R_2$ is H, an amino group or a lower alkyl group having from one to four carbon atoms; and $R^7$ is a cyclopropyl group or a nitrogen-containing heterocyclic group, which each may be substituted by one or more substituents.

The nitrogen-containing heterocyclic group of formula (II) may be a piperazinyl group, a pyrrolidinyl group, a piperidinyl group or a pyridyl group which may be substituted by one or more substituents.

Preferably said nitrogen-containing heterocyclic group is of the general formulae:

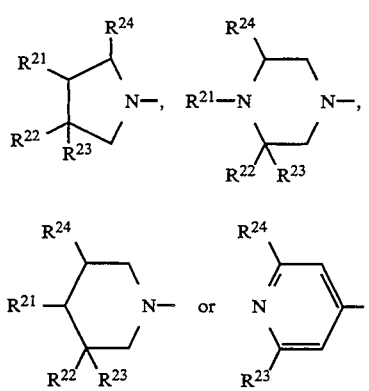

wherein $R^{21}$, $R^{22}$, $R^{23}$ and $R^{24}$ each independently is a hydrogen atom, a halogen atom, an amino group, a lower alkyl group, a lower alkoxyl group, an amino-lower alkyl group, a lower alkylamino group, a di-lower alkylamino group or a lower alkylamino-lower alkyl group, and wherein two may be combined with each other to form an additional ring.

More preferably, said nitrogen-containing heterocyclic group is a group of the general formulae:

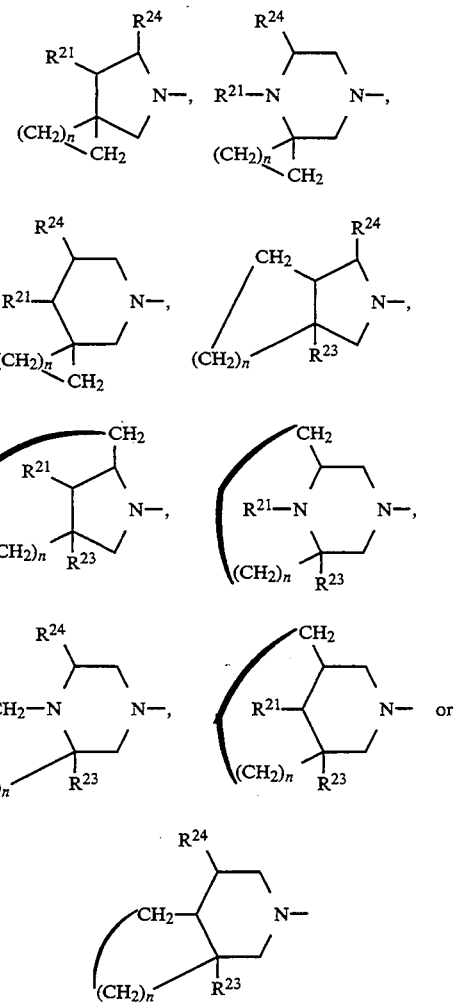

wherein $R^{21}$, $R^{23}$ and $R^{24}$ each independently is a hydrogen atom, a halogen atom, an amino group, a lower alkoxyl group, an amino-lower alkyl group, a lower alkylamino group, a di-lower alkylamino group or a lower alkylamino-lower alkyl group; and n is 0, 1, 2 or 3.

Specific examples of said nitrogen-containing heterocyclic group of formula (II) are 3-aminopyrrolidinyl, 3-methylaminopyrrolidinyl, 3-dimethylaminopyrrolidinyl, 3-ethylaminopyrrolidinyl, 3-propylaminopyrrolidinyl, 3-isopropylaminopyrrolidinyl, 3-amino-4-methylpyrrolidinyl, 3-amino-5-methylpyrrolidinyl, 3-amino-4,5-dimethylpyrrolidinyl, 3-methylamino-4-methylpyrrolidinyl, 3-methylamino-5-methylpyrrolidinyl, 3-methylamino-4,5-dimethylpyrrolidinyl, 3-dimethylamino-4-methylpyrrolidinyl, 4-amino-3,3-dimethylpyrrolidinyl, 3-dimethylamino-5-methylpyrrolidinyl, 3-dimethylamino-4,5-dimethylpyrrolidinyl, piperazinyl, 3-methylpiperazinyl, 4-methylpiperazinyl, 3,4-dimethylpiperazinyl, 3,5-dimethlpiperazinyl, 3,4,5-trimethylpiperazinyl, 4-ethyl-3,5,dimethylpiperazinyl, 4-isopropyl-3,5-dimethylpiperazinyl, 4-isopropyl-3,5-dimethylpiperazinyl, 3-aminomethylpyrrolidinyl, 3-methylaminomethylpyrrolidinyl, 3-(1-amino)ethylpyrrolidinyl, 3-(1-methylamino)ethylpyrrolidinyl, 3-(1-ethylamino)ethylpyrrolidinyl, 3-(1-amino)propylpyrrolidinyl, 3-(1-methylamino)propylpyrrolidinyl, 3-amino-4,4-dimethylpyrrolidinyl, 7-amino-5-azaspiro[2.4]-heptan-5-yl, 8-amino-6-azaspiro [3.4]octan-6-yl, 1,4-diazabicyclo[3.2.1]octan-4-yl, 3,8-diazabicyclo[3.2.1]octan-3-yl, 8-ethyl-3,8-diazabicyclo[3.2.1]octan-3-yl, 8-methyl-3,8-diazobicyclo[3.2.1]octan-3-yl and 4-(5-methyl-2-oxo-1,3-dioxolen-4-yl)methyl-1-piperadinyl.

As to the antimycotic agent which is used with the pyridonecarboxylic acid derivatives in the practice of the instant invention to yield excellent antimycotic activity, the art recognizes a variety of compounds with antimycotic activity, see for example, The Merck Index, latest edition.

For example, antibiotics, such as polyene-type antibiotics, such as amphotericin B (U.S. Pat. No. 2,908,611), or other varieties, such as griseofulvin (U.S. Pat. No. 3,069,239), azoles, such as triazole compounds, such as fluconazole (U.S. Pat. No. 4,404,216) and itracozole (U.S. Pat. No. 4,267,179) and imidazole compounds, such as, miconazole (U.S. Pat. No. 3,717,655) and ketoconazole (U.S. Pat. No. 4,144,346); allylamine compounds, such as, naftifin (U.S. Pat. No. 4,282,251) and terbinafine (EP-024587-A); and other antifungal compounds, such as flucytosine (U.S. Pat. No. 3,040,026).

The dosages of the antimycotic agents generally are known in the art. For example, the usual dose of fluconazole is 50–400 mg/day i.v. and the dose of amphotericin B varies based on route being, 0.25–1.0 mg/kg body weight per day i.v., 10–20 mg/day endotracheally, 5–20 mg/day endoperitoneally, 15–40 mg/day intravesically and 2.5–5 mg/ml taken 2–5 times per day by inhalation. Reference may be made to the latest edition of the Physician's Desk Reference.

It is preferred that the agents of the instant invention be administered orally or intravenously. Preferred dosages are about 50–1000 mg/day and more preferably 50–400 mg/day. The daily dosages can be administered in a single bolus or divided up to 4 times a day. For example, DU-6859a can be administered at a rate of 400 mg per day, wherein the 400 mg can be divided into two doses of 200 mg each given at two different times a day or at a rate of 300 mg per day given in three equal 100 mg doses taken at three different times per 24 hour period.

The pyridonecarboxylic acid derivative and the antimycotic agent can be administered simultaneously or sequentially and separately. Moreover, the pyridonecarboxylic acid derivative and antimycotic agent can be formulated into a single product or maintained separately as distinct formulations. A preferred route of administration is to first administer the antimycotic agent to obtain effective blood levels thereof and then to administer a pyridonecarboxylic acid derivative.

Hence, it is contemplated that the pyridone carboxylic acid derivative and antimycotic agent can be configured in a number of ways to enable a simultaneous, sequential or separate administration. For example, the two active ingredients can be presented in a kit comprising at least two containers, each of which comprises one of the two active ingredients.

Alternatively, each of the active ingredients can be encapsulated, encased or included in or within microspheres using known methods and the two forms of microspheres can be maintained in separate containers, admixed in a single bulk container or admixed within a capsule for administration, for example. In a preferred embodiment, to assure a suitable blood level of the antimycotic agent, the microcapsules can be configured to dissolve or dissipate at different rates so that the antimycotic agent is released before the pyridonecarboxylic acid derivative is.

The pyridonecarboxylic acid derivative and antimycotic agent of the instant invention are active on various pathogenic fungi. Illustrative examples of fungi which are treatable with the compounds of the instant invention include species of the genera, Cryptococcus, Candida, Torulopsis, Trichosporon, Aspergillus, Bipolaris, Fusarium, Trichophyton, Sporothrix, Pseudallescheria, Schedosporium, Coccidioides, Histoplasma, Blastomyces and the like.

Representative species include *Cryptococcus neoformans, Candida albicans, Candida tropicalis, Torulopsis glabrata, Trichosporon beigelii, Aspergillus fumigatus, Aspergillus flavus, Trichophyton mentagrophytes, Trichophyton rubrum, Sporothrix schenckii, Pseudallescheria boydii, Schedosporium apiospermum, Coccidioides immitis, Histoplasma capsulatum* and *Blastomyces dermatitidis.*

Because such combinations of the instant invention often yield additive or synergistic effects, the respective amounts of any active agent component of the mixture can be reduced relative to the effective dosage when used alone. The dosage reduction can be ascertained by known methods, such as a checkerboard synergism titration protocol (Pfaller et al. (1988) J. Clin. Micro. 26:1437; Galgiani et al. (1992); J. Med. Vet. Mycol.; Pfaller et al. (1990) Antimicrob. Ag. Chemother. 34:1648; "Antibiotics in Laboratory Medicine" (1991) Lorian, ed., 3rd. ed., Williams & Wilkins, Baltimore, Md.). Such protocols and experimentation enables, for example, a comparison of minimum inhibitory (MIC) and minimum lethal (MLC) concentrations of agents used alone and in combination, at varying concentrations.

It will be appreciated that the practice of the instant invention can be implemented at the in vitro and in vivo levels and at the level of single cells, such as animal cell cultures or bacteria, of cell aggregates, of tissues, of organs and of organisms. Hence, in the context of the instant invention, a biologic host can be a cell, a tissue, an organ, an organism and so on.

Moreover, the effective level of an antimycotic agent may be ascertained in the cell, in the surrounding medium or fluid, or in the circulatory system of an organism, for example, prior to use of a pyridonecarboxylic acid derivative so as to achieve an enhanced effect of said antimycotic agent.

The methods for ascertaining the presence and amount of an antimycotic agent prior to use of a pyridonecarboxylic acid derivative are those known in the art and practiced to determine such levels, for example, in a clinical hospital laboratory where it is desirable to determine whether effective blood levels of a drug have been achieved under the dosing regimen in place.

Non-limiting Formulation Examples are given below for illustrative purposes only.

| FORMULATION EXAMPLE 1 | |
|---|---|
| Capsule: | |
| Compound of Example 1 | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| total: | 150.0 mg |
| FORMULATION EXAMPLE 2 | |
| Solution: | |

-continued

| | |
|---|---|
| Compound of Example 1 | 1 to 10 g |
| Acetic acid or sodium hydroxide | 0.5 to 2 g |
| Ethyl p-hydroxybenzoate | 0.1 g |
| Purified water | 87.9 to 98.4 g |
| total: | 100 g |

FORMULATION EXAMPLE 3

Powder for Admixture with Feedstuff:

| | |
|---|---|
| Compound of Example 1 | 1 to 10 g |
| Corn starch | 89.5 to 98.5 g |
| Light anhydrous silicic acid | 0.5 g |
| total: | 100 g |

The instant invention now is illustrated in greater detail by way of the following Examples, but it should be understood that the instant invention is not deemed to be limited to the Examples.

EXAMPLE 1

(−)-7-(7-Amino-5-azaspiro[2.4]heptan-5-yl)-8-chloro-6-fluoro-1-(1,2-cis-2-fluoro-1-cyclopropyl)-1,4-dihydro-4-oxoquinoline-3-carboxylic acid (26bb):

To 255 mg of 7-(7-t-butoxycarbonylamino-5-azaspiro[2.4]heptan-5-yl)-8-chloro-6-fluoro-1-(1,2-cis-2-fluoro-1-cyclopropyl)-1,4-dihydro-4-oxoquinoline-3-carboxylic acid (25bb) were added 0.5 ml of anisole and 10 ml of trifluoroacetic acid on ice. After warming to room temperature, the mixture was stirred for 30 minutes. The solvent was removed under reduced pressure and a 1N sodium hydroxide aqueous solution was added to the residue adjusting the pH to 11 to 12.

The alkaline aqueous solution was washed twice with chloroform. The aqueous layer was adjusted to a pH of about 7 with concentrated hydrochloric acid and a 10% citric acid aqueous solution and extracted three times with chloroform. The extract was washed with water and dried over anhydrous sodium sulfate. The solvent was removed under reduced pressure and the resulting solid was recrystallized from ethanol-concentrated aqueous ammonia to obtain 142 mg of the titled compound (26bb) as a colorless crystal.

Melting Point: 127°–140° C. (with decomposition)
Elemental Analysis for $C_{19}H_{18}N_3O_3F_2Cl \cdot \frac{1}{4}H_2O$
Calcd. (%): C 55.08; H 4.50; N 10.14
Found (%): C 54.86; H 4.80; N 10.03

The titled compound is named correctly (−)-7-(7-(S)-amino-5-azaspiro[2.4]heptan-5-yl)-8-chloro-6-fluoro-1-[2-(S)-2-fluoro-1-(R)-cyclopropyl]-4-oxo-1,4-dihydroquinoline-7-carboxylic acid.

Recrystallization of the compound obtained in aqueous ethanol gave another crystal showing the following physical data.

Melting Point: 127.3°–135.5° C.
Elemental Analysis for $C_{19}H_{18}N_3O_3F_2Cl \cdot 3/2H_2O$:
Calcd. (%): C 52.23; H 4.85; N 9.61
Found (%): C 52.16; H 4.70; N 9.53

EXAMPLE 2

Checkerboard synergy studies were accomplished via a macrobroth dilution procedure employing combination of DU-6859a plus amphotericin B (AMB), fluconazole (FLU) and miconazole (MON) against strains of *Candida spp.* (25 strains), *Cryptococcus neoformans* (10), *Torulopsis glabrata* (5) Aspergilli (10), *Blastomyces dermatitidis* (5), *Coccidioides immitis* (5), *Histoplasma capsulatum* (5), *Sporothrix schenckii* (3), *Bipolaris spp.* (5), *Fusarium spp.* (5), *Pseudallescheria boydii* (3) and *Trichophyton spp.* (6).

Inocula for testing of yeasts were prepared spectrophotometrically while mold inocula were prepared via hemacytometer counts. Minimum inhibitory and minimum lethal concentrations (MIC/MLC) were read visually at the time of positivity of a growth control tube.

| Candida | AMB Alone | AMB + DU-6859a | FLU Alone | FLU + DU-6859a | MON Alone | MON + DU-6859a |
|---|---|---|---|---|---|---|
| *C. albicans* | MLC >4.62 | Synergy 1.16 + 0.39 | MIC 2.5 | Synergy 0.3 + 0.78 | MIC 1.25 | Synergy ≦0.15 + 0.78 |
| Cryptococcus | MIC 0.29 | Synergy 0.07 + 0.39 | MIC 10 | Additivism 5 + 0.78 | MLC 5 | Synergy 1.25 + ≦0.19 |
| *Blastomyces dermatitidis* | MIC 0.29 | Synergy 0.07 + 0.78 | MIC 10 | Indifferent 10 + ≦0.19 | MLC 5 | Synergy 0.6 + ≦0.19 |

All references cited herein are herein incorporated by reference in entirety thereof.

While the invention has been described in detail and with reference to specific embodiments thereof, it will be apparent to one skilled in the art that various changes and modifications can be made therein without departing from the spirit and scope thereof.

What is claimed is:

1. A method for enhancing the antimycotic effect of an antimycotic agent comprising administering to a biologic host carrying said antimycotic agent an antimycotic enhancing amount of (−)-7-(7-(S)-amino-5-azaspiro[2.4]heptan-5-yl)-8-chloro-6-fluoro-1-[2-(S)-fluoro-1-(R)-cyclopropyl]-4-oxo-1,4-dihydroquinoline-7-carboxylic acid or sesquihydrate thereof.

2. The method of claim 1, wherein said biologic host is administered to an antimycotic enhancing amount of (−)-7-(7-(S)-amino-5-azaspiro[2.4]heptan-5-yl)-8-chloro-6-fluoro-1-[2-(S)-fluoro-1-(R)-cyclopropyl]-4-oxo-1,4-dihydroquinoline-7-carboxylic acid sesquihydrate.

* * * * *